United States Patent [19]

Lai et al.

[11] Patent Number: 5,420,324
[45] Date of Patent: May 30, 1995

[54] FUMARAMIDE SILOXANE HYDROGEL COMPOSITIONS

[75] Inventors: Yu-Chin Lai, Pittsford; Ronald E. Bambury, Fairport, both of N.Y.

[73] Assignee: Bausch & Lomb Incorporated, Rochester, N.Y.

[21] Appl. No.: 295,966

[22] Filed: Aug. 24, 1994

Related U.S. Application Data

[62] Division of Ser. No. 31,428, Mar. 15, 1993, Pat. No. 5,374,662.

[51] Int. Cl.$^6$ ................................................. C07F 7/10
[52] U.S. Cl. ...................................... 556/419; 564/153; 564/160
[58] Field of Search ................ 556/419; 564/153, 160

[56] References Cited

U.S. PATENT DOCUMENTS

| | | | |
|---|---|---|---|
| 3,408,429 | 10/1968 | Wichterle | 264/1 |
| 3,496,254 | 2/1970 | Wichterle | 264/1 |
| 3,808,248 | 4/1974 | Berger et al. | 556/440 |
| 4,084,459 | 4/1978 | Clark | 82/1 |
| 4,153,641 | 5/1979 | Deichert et al. | 260/827 |
| 4,189,546 | 2/1980 | Deichert et al. | 528/26 |
| 4,192,827 | 3/1980 | Mueller et al. | 525/123 |
| 4,197,266 | 4/1980 | Clark et al. | 264/1 |
| 4,260,725 | 4/1981 | Keogh et al. | 526/279 |
| 4,486,577 | 12/1984 | Mueller et al. | 525/474 |
| 4,605,712 | 8/1986 | Mueller et al. | 525/474 |
| 4,954,587 | 9/1990 | Mueller | 526/245 |
| 5,142,009 | 8/1992 | Kawaguchi | 526/245 |
| 5,250,583 | 10/1993 | Kawaguchi et al. | 523/107 |
| 5,310,779 | 5/1994 | Lai | 524/588 |

FOREIGN PATENT DOCUMENTS

| | | |
|---|---|---|
| 0219884 | 4/1987 | European Pat. Off. . |
| 62-39589 | 2/1987 | Japan . |
| 62-50728 | 3/1987 | Japan . |

OTHER PUBLICATIONS

Radical High Polymerization of Dialkyl Fumarates with Bulky Substituents Leading to Less-Flexible Rod-Like Polymers, T. Otsu, H. Minai, N. Toyoda and T. Yasuhara (1985) Makromol. Chem. Suppl., 42, 133-142.

*Primary Examiner*—Mark Nagumo
*Attorney, Agent, or Firm*—Denis A. Polyn; David M. Krasnow; Salvatore P. Pace

[57] ABSTRACT

Fumaramide-containing monomers are disclosed which are especially useful in the preparation of biocompatible devices, especially contact lenses.

1 Claim, No Drawings

FUMARAMIDE SILOXANE HYDROGEL COMPOSITIONS

This is a divisional of application Ser. No. 08/031,428 filed on Mar. 15, 1993, now U.S. Pat. No. 5,374,662.

BACKGROUND OF THE INVENTION

FIELD OF THE INVENTION

The present invention relates to novel fumarate- and polyfumaramide-containing monomers and compositions comprising the monomers. Especially preferred are the polyfumarate- and polyfumaramide-containing compositions used to make highly oxygen permeable hydrogels which may be used to make biomedical devices including contact lenses.

BACKGROUND

In the field of contact lenses, various factors must combine to yield a material that has appropriate characteristics. Polysiloxane materials are useful materials for making contact lenses due to, among other properties, their excellent oxygen permeability. See U.S. Pat. Nos. 4,153,641 and 4,189,546. However, certain polysiloxane materials are known to experience poor wetting.

Difunctional groups such as fumarates and maleates are known to be viable wetting comonomers in certain polysiloxane copolymeric systems. However, it is well known by those skilled in the field that fumarates often do not easily polymerize into high molecular weight polymers due to steric hindrance.

Certain bulky siloxane-containing fumarates, including bis(siloxanylalkyl)fumarate and (poly)alkylfluoroalkyl fumarates, reportedly may be used as copolymers to make hard contact lens materials. (See European Patent Application No. 86114829.4.) However, the known polymerization schemes for such fumarate-containing polymers, which are directed exclusively to hard contact lens materials, require a minimum of at least 24 hours of curing, and achieve only a low yield of the desired polymer.

SUMMARY OF THE INVENTION

In accordance with the present invention novel wettable fumarate- and fumaramide-containing monomers are disclosed for use with both silicone and non-silicone containing polymeric systems used for biomedical devices, especially contact lenses. The novel monomers have the following schematic representations:

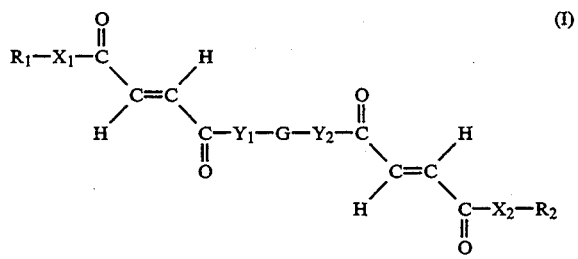

(I)

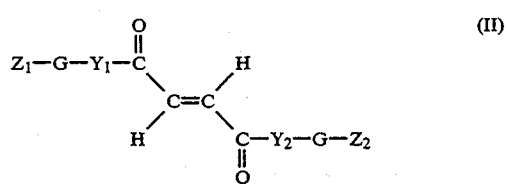

(II)

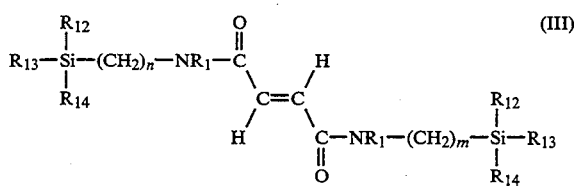

(III)

wherein

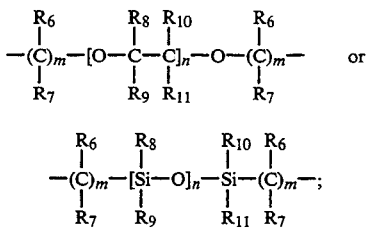

$X_1$, $X_2$, $Y_1$ and $Y_2$ are independently O or $NR_4$, except that when G is siloxane-containing, $X_1$ and $X_2$ must be $NR_4$;

$Z_1$ and $Z_2$ are independently $OR_3$ or $NR_4R_5$;

$R_1$, $R_2$, $R_3$, $R_4$ and $R_5$ are independently H or an alkyl group having 1 to 10 carbon atoms;

$R_6$, $R_7$, $R_8$, $R_9$, $R_{10}$ and $R_{11}$ are independently hydrogen or an alkyl-containing or fluoroalkyl-containing group having 1 to 10 carbon atoms which may have ether linkages between two carbon atoms;

$R_{12}$, $R_{13}$ and $R_{14}$ are independently methyl, trimethylsiloxy or pentamethyldisiloxanyloxy;

m is 1 to 10; and n is 5 to 100.

DETAILED DESCRIPTION OF THE INVENTION

The ease with which the fumarate- and fumaramide-containing monomers of this invention are polymerized into useful polymers was unexpected. The monomer mixes containing the fumarate- and fumaramide-containing monomers are able to be cured within approximately two to four hours which is significantly faster than any known fumarate containing systems. The novel fumarate monomers of the present invention, therefore enable the attributes of fumarate chemistry to be used in new fields.

While the present invention contemplates the use of novel fumarate- and fumaramide-containing polymers for both "hard" and "soft" contact lenses, the formulations containing the fumarate- and fumaramide-containing monomers of the present invention are thought to be especially useful as soft hydrogel contact lenses. As is understood in the field, a lens is considered to be "soft" if it can be folded back upon itself without breaking.

A hydrogel is a hydrated cross-linked polymeric system that contains water in an equilibrium state. Silicone hydrogels (i.e., hydrogels containing silicone) are usually prepared by polymerizing a mixture containing at least one silicone-containing monomer and at least one hydrophilic monomer. Either the silicone-containing monomer or the hydrophilic monomer may function as a crosslinking agent (a crosslinker), being defined as a monomer having multiple polymerizable functionalities. Additional crosslinkers also may be present in the monomer mix which polymerizes to form the hydrogel.

The fumarate- and fumaramide-containing monomers of the present invention have at least one fumarate or fumaramide group. Monomer mixes comprising the novel monomers of the present invention may comprise both thermal- and photoinitiators for curing purposes. The monomer mixes may further comprise at least one additional hydrophilic monomer. Further, the monomer mix may additionally comprise at least one siloxane-containing monomer.

In further embodiments of the present invention, the novel monomers are used to make biomedical devices and are useful in formulations for silicone-containing and non-silicone-containing contact lenses which may be either "soft" or "hard" and which may preferably be hydrogels.

As is known in the field, certain crosslinked polymeric materials may be polymerized to form a hard water-free xerogel. Xerogels are understood to be unhydrated hydrogel formulations. It was found that such xerogels could be physically altered to, for example, impart optical properties through machining, and then be hydrated and retain their water content.

When the term "polymerization" is used herein we refer to the polymerization of the double bonds of the monomers and prepolymers endcapped with polymerizable unsaturated groups which results in a crosslinked three dimensional network.

Further, notations such as "(meth)acrylate" or "(meth)acrylamide" are used herein to denote optional methyl substitution. Thus, for example, methyl (meth)acrylate includes both methyl acrylate and methyl methacrylate and N-alkyl(meth)acrylamide includes both N-alkyl acrylamide and N-alkyl methacrylamide.

The term "prepolymer" denotes a high molecular weight monomer containing polymerizable groups. The monomers added to the monomeric mixture of the present invention may therefore be monomers or prepolymers. Thus, it is understood that the term "silicone-containing monomers" includes "silicone-containing prepolymers".

The terms "shaped articles for use in biomedical applications" or "biomedical devices or materials" or "biocompatible materials" mean the hydrogel materials disclosed herein have physicochemical properties rendering them suitable for prolonged contact with living tissue, blood and the mucous membranes.

The fumarate- and fumaramide-containing monomers of the present invention may be prepared according to syntheses well-known in the art and according to the methods disclosed in the following examples.

As mentioned previously, additional silicone-containing monomers may be present in the monomer mixes with the fumarate or fumaramide-containing monomers. One preferred class of suitable silicone-containing monomers which may be incorporated into a monomer mix with the fumarate or fumaramide-containing monomers of the present invention are the bulky polysiloxanylalkyl (meth)acrylic monomers represented by the following formula (IV):

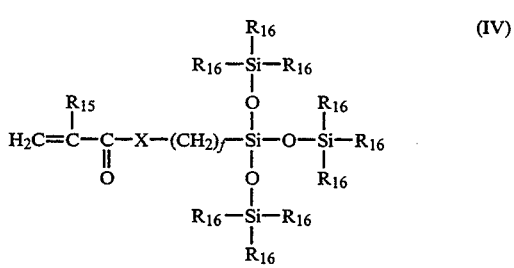

wherein:

X is O or NR;

each $R_{15}$ is independently hydrogen or an alkyl group having 1 to 10 carbon atoms; and each $R_{16}$ is independently a lower alkyl or phenyl group; and f is 1 or 3 to 10.

Such bulky monomers include methacryloxypropyl tris(trimethylsiloxy)silane, pentamethyldisiloxanylmethylmethacrylate, tris(trimethylsiloxy)methacryloxy propylsilane, phenyltetramethyldisiloxanylethyl acetate, and methyldi(trimethylsiloxy)methacryloxymethyl silane.

A further preferred class of silicone-containing monomers which may be incorporated into a monomer mix with the fumarate- or fumaramide-containing monomers of the present invention are the poly(organosiloxane) monomers represented by the following formula (V):

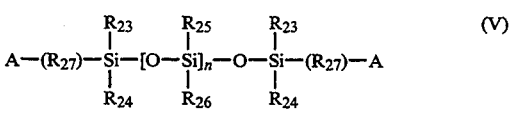

wherein:

A is an activated unsaturated group, such as an ester or amide of an acrylic or a methacrylic acid;

each $R_{23}$-$R_{26}$ is independently selected from the group consisting of a monovalent hydrocarbon radical or a halogen substituted monovalent hydrocarbon radical having 1 to 18 carbon atoms which may have ether linkages between carbon atoms;

$R_{27}$ is a divalent hydrocarbon radical having from 1 to 22 carbon atoms; and n is 0 or an integer greater than or equal to 1.

Further, hydrophilic monomers may also be incorporated into the monomer mixes to form hydrogels. Such preferred hydrophilic monomers may be either acrylic- or vinyl-containing monomers. Such hydrophilic monomers may be used as crosslinking agents. The term "vinyl-type" or "vinyl-containing" monomers refers to non-acrylic monomers containing the vinyl grouping ($CH_2=CH_2$). Such hydrophilic vinyl-containing monomers are known to polymerize relatively easily. "Acrylic-type" or "acrylic-containing" monomers are those monomers containing the acrylic group

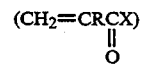

wherein R=H or $CH_3$ and X is O or NH.

When siloxane-containing monomers are incorporated into the monomer mix, the weight % of the siloxane-containing monomers as compared to the total monomer mix weight % is from about 5% to 80%, more preferably from about 20% to 75%, and most preferably 40% to 70%. The relative weight % of hydrophilic monomer(s) to total weight % of the comonomer mix is preferably from about 5% to 80%, more preferably from about 20% to 70%, and most preferably 30% to 60%.

Preferred hydrophilic vinyl-containing monomers which may be incorporated into the hydrogels of the present invention include monomers such as N-vinyl lactams (e.g. N-vinyl pyrrolidone (NVP)), N-vinyl-N-methyl acetamide, N-vinyl-N-ethyl acetamide, N-vinyl-N-ethyl formamide, N-vinyl formamide, with NVP being the most preferred.

Preferred hydrophilic acrylic-containing monomers which may be incorporated into the hydrogel of the present invention include hydrophilic monomers such as N,N-dimethyl acrylamide (DMA), 2-hydroxyethyl methacrylate, glycerol methacrylate, 2-hydroxyethyl methacrylamide, methacrylic acid and acrylic acid, with DMA being the most preferred.

When it is desirable for both an acrylic-containing wetting monomer and a vinyl-containing wetting monomer to be incorporated into the silicone-containing polymer of the present invention, a further crosslinking agent having both a vinyl and an acrylic polymerizable group may be used, since these vinyl and acrlyic wetting monomers have greatly differing reactivity ratios and do not copolymerize efficiently. Such crosslinkers which facilitate the copolymerization of these monomers are the subject of presently co-pending and commonly assigned U.S. patent application No. 07/922,452 filed Jul. 30, 1992, now U.S. Pat. No. 5,310,779. Such crosslinkers are represented by the following schematic representation:

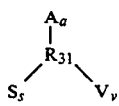

wherein

V denotes a vinyl-containing group having the formula:

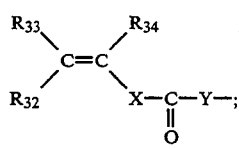

A denotes an acrylic-containing group having the formula:

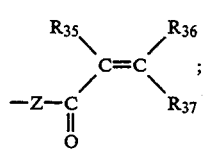

S denotes a styrene-containing group having the formula:

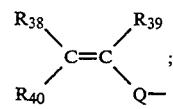

wherein $R_{31}$ is an alkyl radical derived from substituted and unsubstituted hydrocarbons, polyalkylene oxide, poly(perfluoro) alkylene oxide, dialkyl-capped polydimethylsiloxane, dialkyl-capped polydimethylsiloxane modified with fluoroalkyl or fluoroether groups;

$R_{32}$-$R_{40}$ are independently H, or alkyl of 1 to 5 carbon atoms;

Q is an organic group containing aromatic moleties having 6–30 carbon atoms;

X, Y, and Z are independently O, NH or S;

v is 1, or higher; and a, s are independently greater than or equal to 0; and a+s is greater than or equal to 1.

Such crosslinkers help to render the monomer mix totally UV-curable. It was further discovered that the use of UV intiators in the monomer mix allowed the fumarate- and fumaramide-containing monomer mixes to cure at surprisingly and unexpectedly rapid rates. This enhanced curing rate is thought to apply to fumarate- and fumaramide-containing monomers which are beyond the scope of the present application. The enhanced curing of fumarates and fumaramides is the subject of a concurrently filed and commonly assigned U.S. patent application (which has not yet received a U.S. Ser. No., but which corresponds to Attorney Docket) No. P01050.

Other crosslinking agents which may be incorporated into the silicone-containing hydrogel of the present invention include polyvinyl, typically di- or tri-vinyl monomers, most commonly the di- or tri(meth)acrylates of dihydric ethylene glycol, triethylene glycol, butylene glycol, hexane-1,6-diol, thio-diethylene glycol-diacrylate and methacrylate; neopentyl glycol diacrylate; trimethylolpropane triacrylate and the like; N, N'-dihydroxyethylene-bisacrylamide and -bismethacrylamides; also diallyl compounds like diallyl phthalate and triallyl cyanurate; divinylbenzene; ethylene glycol divinyl ether; and the (meth)acrylate esters of polyols such as triethanolamine, glycerol, pentanerythritol, butylene glycol, mannitol, and sorbitol. Further, illustrations include N, N-methylene-bis-(meth)acrylamide, sulfonated divinylbenzene, and divinylsulfone. Also useful are the reaction products of hydroxyalkyl (meth)acrylates with unsaturated isocyanates, for example the reaction product of 2-hydroxyethyl methacrylate with 2-isocyanatoethyl methacrylate (IEM). See U.S. Pat. No. 4,954,587.

Other known crosslinking agents are polyether-bisurethane-dimethacrylates (see U.S. Pat. No. 4,192,827), and those crosslinkers obtained by reaction of polyethylene glycol, polypropylene glycol and polytetramethylene glycol with 2-isocyanatoethyl methacrylate (IEM) or m-isopropenyl-dimethylbenzyl isocyanates (m-TMI), and polysiloxane-bisurethane-dimethacrylates. See U.S. Pat. Nos. 4,486,577 and 4,605,712. Still other known crosslinking agents are the reaction products of polyvinyl alcohol, ethoxylated polyvinyl alcohol or of polyvinyl alcohol-co-ethylene with 0.1 to 10 mol % vinyl isocyanates like IEM or m-TMI.

The monomers of the present invention, when copolymerized, are readily cured to cast shapes by methods such as UV polymerization, use of free radical thermal initiators and heat, or combinations thereof. Representative free radical thermal polymerization initiators are organic peroxides, such as for example acetal peroxide, lauroyl peroxide, decanoyl peroxide, stearoyl peroxide, benzoyl peroxide. tertiary butyl peroxypivalate, peroxydicarbonate, and the commercially available thermal initiators such as Lupersol 256, 225 and the like, employed in a concentration of about 0.01 to 2 percent by weight of the total monomer mixture. Representative UV initiators are those known in the field such as, benzoin methyl ether, benzoin ethyl ether, Darocur-1173, 1164, 2273, 1116, 2959, 3331 (EM Industries) and Igracure 651 and 184 (Ciba-Geigy).

In addition to the above-mentioned polymerization initiators, the copolymer of the present invention may also include other monomers as will be apparent to one skilled in the art. For example, the monomer mix may include additional colorants, or UV-absorbing agents and toughening agents such as those known in the contact lens art.

The resulting copolymers of this invention can be formed into contact lenses by the spincasting processes such as those disclosed in U.S. Pat. Nos. 3,408,429 and 3,496,254 and other conventional methods, such as compression molding as disclosed in U.S. Pat. Nos. 4,084,459 and 4,197,266.

Polymerization of the monomer mix may be conducted either in a spinning mold, or a stationary mold corresponding to a desired contact lens shape. The thus-obtained contact lens may be further subjected to a mechanical finishing, as occasion demands. Also, the polymerization maybe conducted in an appropriate mold or vessel to give a lens material in the form of button, plate or rod, which may then be processed (e.g., cut or polished via lathe or laser) to give a contact lens having a desired shape.

The hydrogels produced by the present invention are oxygen transporting, hydrolytically stable, biologically inert, and transparent. The monomers and prepolymers employed in accordance with this invention, are readily polymerized to form three dimensional networks which permit the transport of oxygen and are optically clear, Strong and hydrophilic.

The present invention provides materials which can be usefully employed for the fabrication of prostheses such as heart valves and intraocular lenses, as optical contact lenses or as films. More particularly, the present invention concerns contact lenses.

The present invention further provides articles of manufacture which can be used for biomedical devices, such as, surgical devices, heart valves, vessel substitutes, intrauterine devices, membranes and other films, diaphragms, surgical implants, blood vessels, artificial ureters, artificial breast tissue and membranes intended to come into contact with body fluid outside of the body, e.g., membranes for kidney dialysis and heart/lung machines and the like, catheters, mouth guards, denture liners, intraocular devices, and especially contact lenses.

It is known that blood, for example, is readily and rapidly damaged when it comes into contact with artificial surfaces. The design of a synthetic surface which is antithrombogenic and nonhemolytic to blood is necessary for prostheses and devices used with blood.

The following examples serve only to further illustrate aspects of the present invention and should not be construed as limiting the invention.

EXAMPLE 1

Preparation of bis-3-(trimethylsiloxyl)silyl propyl fumaramide.

Dry, basic alumina (11.48 g), 3-aminopropyl tris(-trimethylsiloxy)silane (7.375 g, 0.02 mol) and 30 mL of methylene chloride were added into a dry 250 mL round bottom flask equipped with a mechanical stirrer and nitrogen blanket. The mixture was cooled with an ice bath at 0–5 degrees C. Fumaryl chloride (1.527 g, 0.01 mol) was then added over a period of two hours while the mixture was kept cold. The solution was then extracted twice with 2N HCl, then twice with 60 mL 0.5N NaOH, followed by 60 mL water (three times). The solution was then concentrated and eluted through silica gel column with a 20:80 methylene chloride:methanol solution. The purified named product was recovered by evaporating the solvent yielding 0.8 g. The purified product melted at 172–174 degrees C. $H^1$-NMR gave the following peaks: 0.05 ppm (singlet, 4H); 2.30 ppm (multiplet, 4H); 1.40 ppm (multiplet, 4H); 3.12 ppm (multiplet, 4H); 6.72 ppm (singlet, 2H); and 6.90 ppm (singlet, 2H). IR gave the peaks characteristic of the structure ($-CH_3$), 1630cm$^{-1}$ (amide I), 1550 cm$^{-1}$ (amide II).

EXAMPLE 2

Preparation of bis(4-hydroxybutyl) tetramethyl disiloxane-based fumarate monomer end-capped with t-butylamine.

Into a 2-neck, 500 mL round bottom flask connected to a nitrogen blanket and reflux condenser was added 6.95 g (0.027 mol.), bis(4-hydroxybutyl) tetramethyldisiloxane, 8.274 g (0.054 mol) of fumaryl chloride and 200 mL of dry toluene. The mixture was brought to 90 degrees C and stirred. After 4 hours, the reaction was found to be complete by checking an aliquot with infrared spectroscopy. The mixture was .vacuum stripped to remove excess fumaryl chloride and toluene at 80 degrees C. The reaction mixture was then cooled and 250 mL of toluene was added. T-butyl amine (9.79 g) was added dropwise while the mixture was cooled to between 0 to 5 degrees C. After the addition of t-butylamine, the temperature was allowed to rise to room temperature. The product mixture was extracted with 0.1N sodium bicarbonate aqueous solution and dried over magnesium sulfate. The liquid product was recovered after vacuum stripping of the solvent. The product crystallized after standing overnight to yield 12.8 g, or 81%.

EXAMPLES 3–4

Preparation of polysiloxanediol-based fumarate prepolymers end-capped with t-butylamine The preparations were conducted as described in Example 2 above except that polysiloxanediols of Mn (molecular weight average) 734 and Mn 1300 were used to prepare monomers designated as "$F_2D_6$" (Example 3) and "$F_2D_{15}$" (Example 4) respectively, instead of bis(4-hydroxybutyl) tetramethyl disiloxane. The designation "Mn" represents the molecular weight average of the polymeric structure. The purified products were clear fluids. IR spectrum (Examples 3 and 4) 3307 cm$^{-1}$, 2982 cm$^{-1}$, 1729 cm$^{-1}$, 1680 cm$^{-1}$, 1643 cm$^{-1}$, 1257 cm$^{-1}$, 1008 cm$^{-1}$, 786 cm$^{-1}$. $H^1$-NMR spectrum (Example 4) 0.08 ppm (Si-CH$_3$); 0.58 ppm (CH2-Si); 1.38 ppm (—CH$_2$—); 1.41 ppm (t-butyl); 1.58 ppm (NH); 1.70 ppm (—C$_H$2—); 4.19 ppm (—CH$_2$); 6.73 ppm (vinyl H).

EXAMPLE 5

Alternate procedure for preparing polysiloxanediol-based fumarate prepolymers end-capped with t-butylamine.

The preparation was conducted in dry tetrahydrofuran (THF) at room temperature for step 1 and in dry THF at 0-5 degrees C at step 2. All other reaction and purification conditions were the same as those described in Example 2.

EXAMPLE 6

Preparation of polysiloxanediol-based fumarate prepolymers end-capped with 3-aminopropyl pyrrolidone.

The preparation was conducted as described in Example 5, using a polysiloxanediol of Mn 1300, and a stoichiometric amount of 3-aminopropyl pyrrolidone in place of the t-butylamine.

EXAMPLE 7

Preparation of polysiloxanediol-based fumarate prepolymer end-capped with 2-hydroxyethyl pyrrolidone.

The preparation of the named product was carried out by the method of Example 6 except that the 3-aminopropyl pyrrolidone was replaced with 2-hydroxyethyl pyrrolidone.

EXAMPLE 8

Preparation of polypropylene glycol-based fumarate prepolymer end-capped with t-butylamine (F$_2$PPG)

A fumarate-containing prepolymer based on polypropylene glycol of Mn 4,000 (PPG-4000) was prepared according to the procedure as described in Example 5 except that the polysiloxanediol was replaced with PPG-4000 in the same stoichiometric amount.

EXAMPLE 9

Preparation of perfluoro polyethylene glycol-based fumarate prepolymer end-capped with t-butylamine.

A fumarate-containing prepolymer based on perfluoro polyethylene glycol (Mn 2000) is prepared according to the method as described in Example 5 except that the polysiloxanediol is replaced by the perfluoro ethylene glycol of the same stoichiometric amount.

EXAMPLE 10

Preparation of bis(hydroxyalkyl)polysiloxanylalkyl fumarate (D$_{12}$)$_2$F.

Into a 2-neck, 500 ml round bottom flask connected to a reflux condenser, a dropping funnel and nitrogen blanket, was added 30.0 g (0.025 mol) of bis(4-hydroxybutyl)polysiloxane (Mn 1,200). Through the dropping funnel, 1.74 g (0.0125 mol) of fumaryl chloride in 20mL of dry toluene was added into the flask over a period of half an hour while the contents in the flask were heated to 80 degrees C and magnetically stirred. The heating was continued for 4 hours. An aliquot was checked with infrared spectroscopy and found to be free of acid chloride. The reaction was stopped and the product was extracted twice with 0.1N sodium bicarbonate and twice with distilled water followed by drying over magnesium sulfate. The final clear fluid product was recovered by removing the toluene under vacuum at 80 degrees C. Yield 26.5 g.

EXAMPLE 11

Film Casting of a fumarate prepolymer

The fumarate prepolymer shown in Example 4 (F$_2$D$_{15}$ end-capped with t-butylamine) was mixed with 1% Lupersol-256, a thermal initiator (*Chemical Name and Source*), and cured between two silane-treated glass plates at 80 degrees C for 20 hours. The released films were extracted with ethanol for 16 hours and then dried in vacuo at 80 degrees C for 16 hours.

EXAMPLE 12

Film casting of fumarate prepolymer with a hydrophilic monomer and hydrophobic monomer into hydrogel films A formulation containing the following was prepared: fumarate prepolymer of Example 2, 70 parts; N,N-dimethylacrylamide (DMA), 30 parts; 1 part Lupersol-256. The resulting clear mix was cured into films between two silane-treated glass plates at 80 degrees C for 20 hours. The released films were then extracted with ethanol for 16 hours, then dried in vacuo at 80 degrees C for 16 hours, followed by boiling water extraction for 4 hours and placed in phosphate buffered saline at pH 7.2.

EXAMPLES 13–19

Film casting of fumarate prepolumer (t-butylamine capped) with hydrophilic monomer and 3-methacryloxypropyl tris(trimethylsiloxy) silane (TRIS).

The following monomer mixes were prepared and cured and processed into hydrogel films according to the procedures of Example 12. Properties of the resultant films are shown below.

| | Examples | | | | | | |
|---|---|---|---|---|---|---|---|
| (Wt %) | 13 | 14 | 15 | 16 | 17 | 18 | 19 |
| Fumarate Formulation | F$_2$D$_6$ | F$_2$D$_6$ | F$_2$D$_{15}$ | F$_2$D$_{15}$ | F$_2$D$_{15}$ | F$_2$PPG | F$_2$D$_{15}$ |
| Fumarate | 70 | 35 | 70 | 35 | 33 | 35 | 25 |
| TRIS | 0 | 35 | 0 | 35 | 33 | 35 | 35 |
| DMA | 30 | 30 | 30 | 30 | 34 | 30 | 30 |
| (D$_{12}$)$_2$F | 0 | 0 | 0 | 0 | 0 | 0 | 10 |

EXAMPLE 20

Film Properties

The fumarate-containing films cast from the formulations of Examples 11–19 were characterized for key properties. The water contents and ethanol extractables for each formulation were determined gravimetrically. The tensile and tear properties were determined in buffered saline, according to the standard ASTM procedures 1708 and 1938 respectively. The oxygen permeabilities were determined by polarographic method with the consideration of edge effect. (See Fatt, Rasson and Melpolder, International Contact Lens Clinic, 14, 389, 1987).

EXAMPLE 21

Contact angle/wettability measurements

The contact angles of the surface of the fumarate films were measured by the captive bubble technique. The films were submerged in buffered saline solution and a bubble of air was attached to the undersurface of the film. The angle created by the intersection of the films and bubble surfaces was measured using a goinometer. The contact angles from cast lenses were also measured similarly. A lower contact angle represents a greater degree of hydrophilicity or surface film wettability.

-continued

| Tear strength (g/mm) | 8.5 |
| --- | --- |

| Properties | Example No. | | | | | | | | |
| --- | --- | --- | --- | --- | --- | --- | --- | --- | --- |
| | 11 | 12 | 13 | 14 | 15 | 16 | 17 | 18 | 19 |
| % extract | — | — | — | — | — | 3.9 | 4.0 | 2.9 | 4.1 |
| % water | 0 | 15 | 19 | 18 | 30 | 21.9 | 24.7 | 26.8 | 20 |
| $O_2$ Perm. Dk | 318 | 7.5 | 100 | 90 | 181 | 138 | 116 | 46 | 137 |
| Cont. angle | 62 | 35 | 30 | 30 | 35 | — | 33 | 31 | 31 |
| Modulus (g/mm$^2$) | 571 | 340 | 960 | 390 | — | 135 | 128 | — | 120 |
| % elong. | 11 | 35 | 12 | 28 | — | 100 | 103 | — | 99 |
| Tear (g/mm) | — | 31 | 2.7 | 4.6 | — | 7.0 | 6.0 | — | 5.5 |

EXAMPLE 22

Hydrolytic stability testing of fumarate hydrogel films

The cured fumarate hydrogel films, after being extracted with solvent and dried in vacuo, were cut into disks weighing 30 mg each, with a thickness of 250 microns. The disks were weighed while dry and then were submerged into buffered saline at pH 7.4 in 12 vials and sealed. After equilibration, the films were placed in an oven at 80 degrees C. Three vials were taken out after 3, 5, 7 and 14 days and the dry weight and water contents were determined gravimetrically. The hydrolytic stabilities were reported as % weight loss over 14 days. Experimentally, it was determined that resultant hydrogels with a weight loss of 7% or less would be considered stable.

The water weight loss and the hydrogel films presented in Example 21 was less than 1.7% in 14 days, indicating the hydrogel films are hydrolytically stable. Separately, the hydrogel films were also subjected to 10 cycles of autoclave cycling at 121 degrees C. Each cycle lasted 30 minutes. There was no change in film appearance.

EXAMPLE 23-26

UV curing of fumarate films

The same fumarate formulations as those in Examples 16-19 were used, except that the thermal initiator was replaced by 1) 0.5 part benzoin methyl ether (BME) (Example 23); 2) 0.2 part BME and 0.5 part Lupersol-225 (Example 24); 3) 0.2 part Darocur-1173 (EM Industries) plus 0.5 part Lupersol-225 (Example 25) and 4) 0.2 part Darocur (Example 26). These formulations were cured between two glass plates and under UV for 2 hours. After curing, the films were processed by the procedures as described in Example 12. The amounts of extractables and water content (%) were as follows:

| | Example No. | | | |
| --- | --- | --- | --- | --- |
| | 23 | 24 | 25 | 26 |
| Initiator | 0.5 BME | 0.2 BME | 0.2 Darocur | 0.2 Darocur |
| Extract. % | 11.5 | 6.8 | 4.6 | 6.2 |
| % Water | 16.5 | 20.5 | 22.2 | 22.0 |

The cured films of the formulation in Example 21 had the following physical properties:

| $O_2$ Permeability | 126 |
| --- | --- |
| Modulus, Dk (G/mm$^2$) | 125 |
| % Elongation | 95 |

EXAMPLE 27

Film casting of t-butylamine-capped $F_2D_{15}$ formulation with higher DMA content A monomer mix containing $F_2D_{15}$, 30 parts; TRIS, 30 parts; DMA 40 parts, and Darocur-1173, 0.2 part was cured under UV for 2 hours and then processed into hydrogel films as described in Example 13. The hydrogel films have the following properties:

| % Extractables | 8.0 | Modulus (g/mm$^2$) | 87 |
| --- | --- | --- | --- |
| % water content | 36 | % Elongation | 140 |
| $O_2$ permeability (Dk) | 77 | Tear strength (g/mm) | 5.1 |

EXAMPLES 28-31

Properties of fumarate hydrogels with N-vinyl pyrrolidone as hydrophilic monomer The following formulations were prepared and cured under UV and then processed into hydrogel films as described in Example 13, with the corresponding hydrogel properties listed below:

| | Example No. | | | |
| --- | --- | --- | --- | --- |
| | 28 | 29 | 30 | 31 |
| Composition | | | | |
| $F_2D_{15}$ | 35 | 30 | 20 | 20 |
| TRIS | 35 | 30 | 30 | 30 |
| NVP | 30 | 40 | 20 | 20 |
| DMA | — | — | 30 | 30 |
| Hexanol | — | — | 20 | 20 |
| Darocur-1173 | 0.2 | 0.2 | 0.2 | 0.2 |
| Lupersol-225 | 0.5 | 0.5 | — | — |
| Physical Properties | | | | |
| % Extract | 5.9 | 11.4 | 4.4 | 1.0 |
| % Water | 17 | 33 | 41 | 41 |
| $O_2$ Perm, Dk | 157 | 113 | 57 | 58 |
| Modulus (g/mm$^2$) | 810 | 621 | 193 | 168 |
| Tear Strength | 7.9 | 6.0 | 4.2 | 3.3 |

EXAMPLES 32-34

Properties of hydrogel films derived from 3-aminopropylpyrrolidone-capped fumarate prepolymer $F_2D_{15}$ and hydrophilic monomers The monomer prepared in Example 6 was used in formulation studies and films were cast as described in Example 28-31, to give hydrogel films with the following properties:

| | Example No. | | |
|---|---|---|---|
| | 32 | 33 | 34 |
| Formulation (parts) | | | |
| $F_2D_{15}$ | 35 | 30 | 30 |
| TRIS | 35 | 40 | 30 |
| DMA | 30 | 30 | 40 |
| Hexanol | 20 | 20 | 20 |
| Darocur-1173 | 0.2 | 0.2 | 0.2 |
| Physical Properties | | | |
| Properties | | | |
| % Extractables | 2.8 | 2.8 | 3.7 |
| % Water | 23.5 | 24.0 | 36.2 |
| $O_2$ Permeability (Dk) | 140 | 135 | 79 |
| Modulus (g/mm$^2$) | 97 | 102 | 76 |
| % Elongation | 100 | 150 | 75 |
| Tear Strength g/mm | 6.9 | 10.4 | 5.0 |

EXAMPLE 35

Cast Molding of $F_2D_{15}$ (T-butylamine-capped)-containing monomer mix into hydrogel lenses The following monomer mix was prepared: fumarate monomer end-capped with t-butylamine, ($F_2D_{15}$, Example 4), 30 parts; TRIS, 30 parts; DMA 40 parts; hexanol, 20 parts; Darocur-1173, 0.2 part. The mix was filtered through a 5-micron filter into a clean vial. Through an applicator, 60-90 microliters of the mix was injected, under an inert nitrogen atmosphere onto a clean plastic mold half and then covered with a second plastic mold half. The molds were then compressed and cured for 90 minutes in the presence of UV light (4200 microwatts). The molds were then opened mechanically and put into a beaker containing aqueous ethanol. The lenses were released from the molds within from 10 minutes to 1 hour. The lenses were then extracted with ethanol for 48 hours, boiled in distilled water for 4 hours and inspected for cosmetic quality and dimension. Lenses passing inspection were thermally disinfected in phosphate buffered saline solution prior to on-eye evaluation.

EXAMPLE 36

Cast Molding of 3-aminopropyl pyrrolidone-capped $F_2D_5$-derived monomer mix into hydrogel lenses The monomer mix of Example 34 was cast-molded and processes into lenses by following the same procedure as described in Example 35.

EXAMPLE 37

Clinical Evaluations

The cast molded polyfumarate hydrogel lenses described in Example 40 were evaluated on six to ten subjects. In each test, a poly(2-hydroxyethyl methacrylate) control lens was worn on one eye and the test lens on the other eye. The lenses were analyzed for wettability and surface deposition after a minimum of 4 hours wear. The polyfumarate lenses displayed excellent wetting equivalent to the poly(HEMA) control lenses. The polyfumate lenses did display more deposits than their poly(HEMA) control counterparts, but were determined to be within an acceptable level.

Many other modifications and variations of the present invention are possible and will be apparent to the skilled practitioner in the field in light of the teachings herein. It is therefore understood that, within the scope of the claims, the present invention can be practiced other than as herein specifically described.

We claim:

1. Fumaramide-containing monomers represented by the schematic representations:

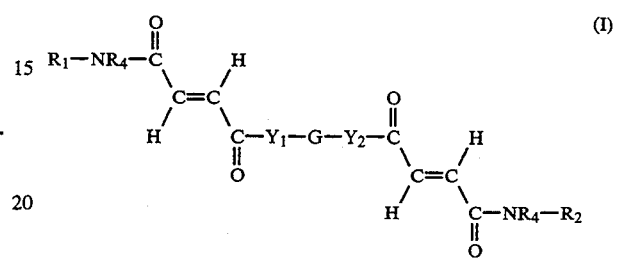

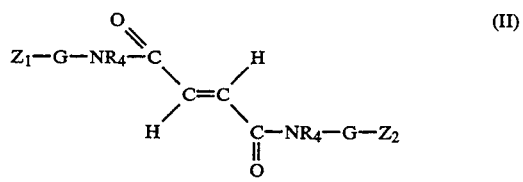

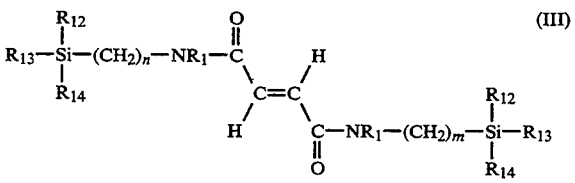

wherein

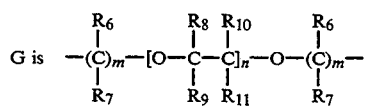

or

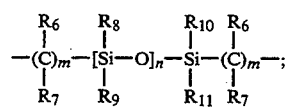

$Y_1$ and $Y_2$ are independently O or $NR_4$;

$Z_1$ and $Z_2$ are independently $OR_3$ or $NR_4R_5$;

$R_1$, $R_2$, $R_3$, $R_4$ and $R_5$ are independently H or an alkyl group having 1 to 10 C atoms;

$R_6$, $R_7$, $R_8$, $R_9$, $R_{10}$ and $R_{11}$ are independently hydrogen, or an alkyl-containing group having 1 to 10 C atoms, or fiuoroalkyl-containing group having 1 to 10 C atoms;

$R_{12}$, $R_{13}$ and $R_{14}$ are independently trimethylsiloxy or pentamethyldisiloxanyloxy;

m is 1 to 10;

n is 5 to 100;

* * * * *

UNITED STATES PATENT AND TRADEMARK OFFICE
CERTIFICATE OF CORRECTION

PATENT NO. : 5,420,324
DATED : May 30, 1995
INVENTOR(S) : Yu-Chin Lai, et al

It is certified that error appears in the above-indentified patent and that said Letters Patent is hereby corrected as shown below:

In column 2, lines 11-15, change

" 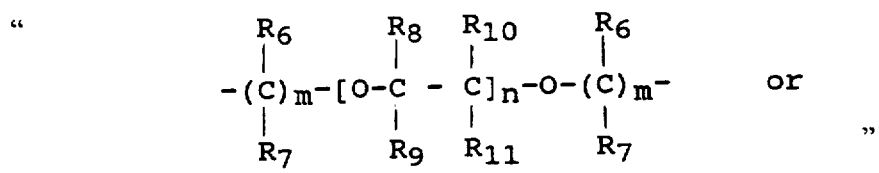 or "

to

-- G is 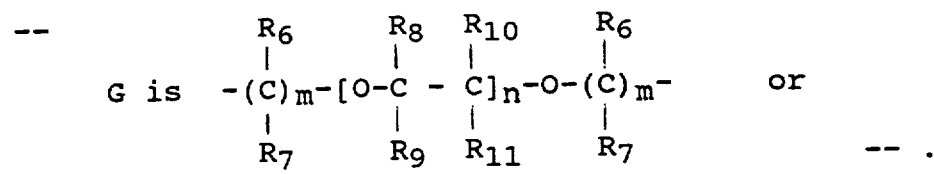 or    -- .

In Column 6, line 62, change "m-isopropenyl-dimethylbenzyl" to read -- m-isopropenyl-ɣ,ɣ-dimethylbenzyl -- .

In Column 10, line 28, change "prepolumer" to read -- prepolymer -- .

UNITED STATES PATENT AND TRADEMARK OFFICE
CERTIFICATE OF CORRECTION

PATENT NO. : 5,420,324

DATED : May 30, 1995

INVENTOR(S) : Yu-Chin Lai, et al

It is certified that error appears in the above-indentified patent and that said Letters Patent is hereby corrected as shown below:

In Column 13, line 47, change "$F_2D_5$" to read -- $F_2D_{15}$ -- .

Signed and Sealed this

Seventeenth Day of October, 1995

*Attest:*

BRUCE LEHMAN

*Attesting Officer*     *Commissioner of Patents and Trademarks*